United States Patent [19]

Szwergold et al.

[11] Patent Number: 5,231,031
[45] Date of Patent: Jul. 27, 1993

[54] METHOD FOR ASSESSING RISK OF DIABETES-ASSOCIATED PATHOLOGIC CONDITIONS AND EFFICACY OF THERAPIES FOR SUCH CONDITIONS

[75] Inventors: Benjamin S. Szwergold, Philadelphia, Pa.; Truman R. Brown, Bedminster, N.J.; Francis Kappler, Philadelphia, Pa.; Aqqaluk Peterson, Copenhagen, Denmark

[73] Assignee: Fox Chase Cancer Center, Philadelphia, Pa.

[21] Appl. No.: 568,919

[22] Filed: Aug. 17, 1990

[51] Int. Cl.⁵ .................. G01N 33/48; G01N 24/08
[52] U.S. Cl. .............................. 436/63; 436/94; 436/104; 436/173; 436/811
[58] Field of Search ............... 436/63, 94, 95, 104, 436/173, 811

[56] References Cited

U.S. PATENT DOCUMENTS 4,906,468  3/1990  Saltiel ............................ 424/85.8

Primary Examiner—James C. Housel
Assistant Examiner—Arlen Soderquist
Attorney, Agent, or Firm—Dann, Dorfman, Herrell and Skillman

[57] ABSTRACT

Concentrations of one or more carbohydrates phosphorylated at a secondary hydroxyl, including fructose-3-phosphate and sorbitol-3-phosphate, in biological tissue or cells of diabetic patients are determined by $^{31}P$ NMR Spectroscopy, High Performance Liquid Chromatography (HPLC) or other appropriate analytical techniques. Elevated levels of such phosphorylated carbohydrates, relative to a prescribed standard or threshold level, are associated with an increased risk for developing the degenerative complications of diabetes. A method is provided for determining the relative concentrations of such phosphorylated carbohydrates, whereby the relative risk of a patient for the development of diabetic complications and the efficacy of therapeutic intervention in prevention of such complications may be assessed.

1 Claim, 6 Drawing Sheets

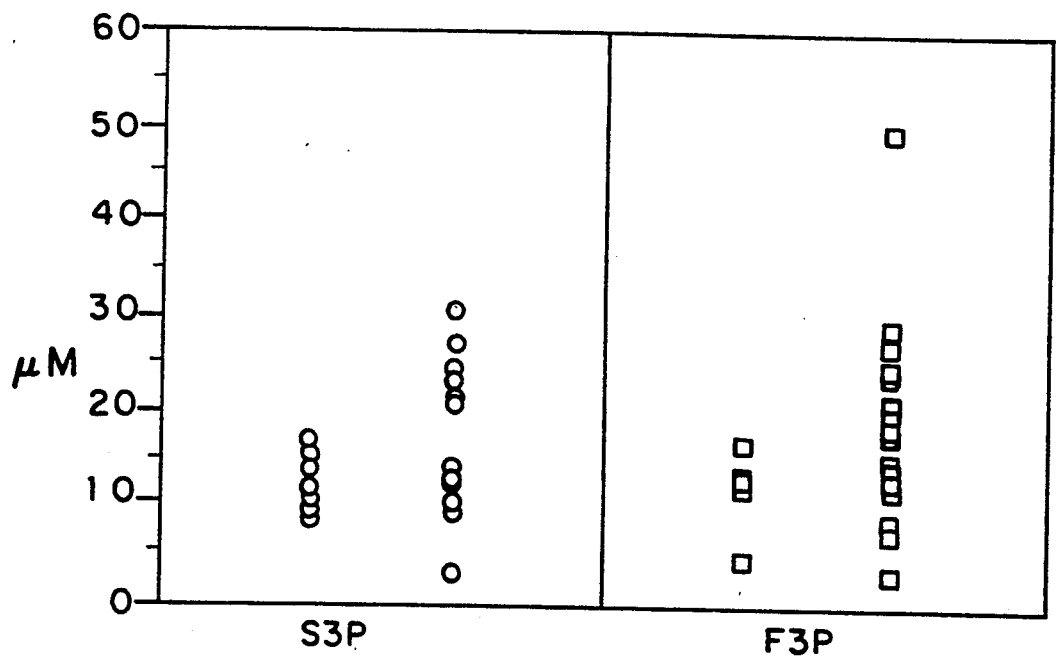
FIG.4A     FIG.4B
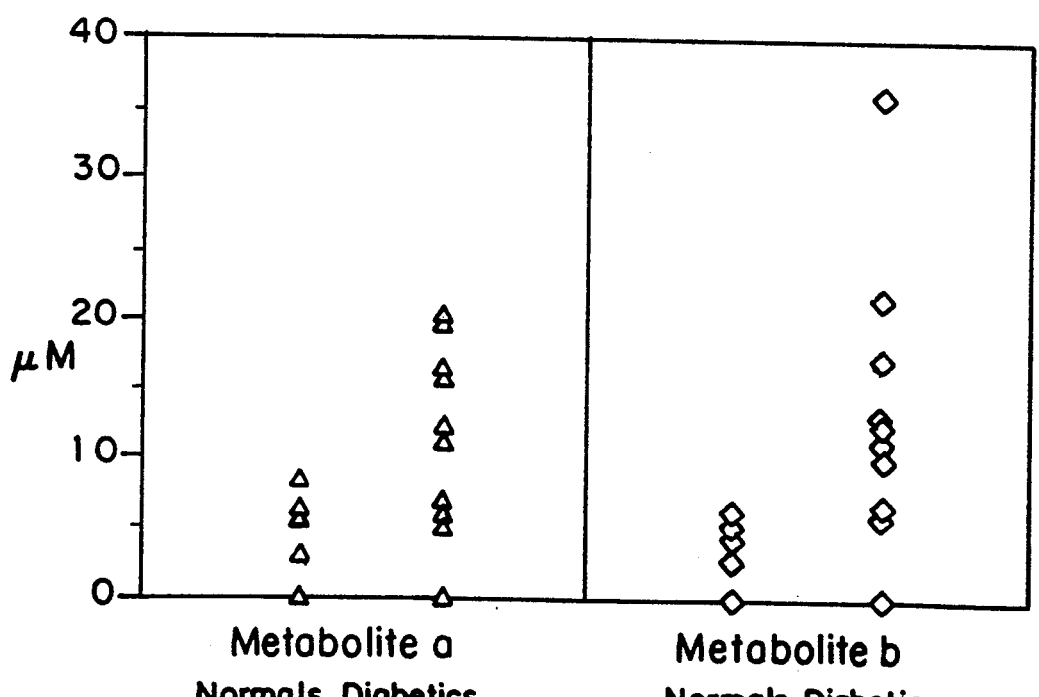
FIG. 4C     FIG.4D

| DIABETIC COMPLICATIONS | METABOLITE RATIO | |
|---|---|---|
| | (a+b)/S3P>1 | (a+b)/S3P<1 |
| YES | 8 | 2 |
| NO | 1 | 6 |

METHOD FOR ASSESSING RISK OF DIABETES-ASSOCIATED PATHOLOGIC CONDITIONS AND EFFICACY OF THERAPIES FOR SUCH CONDITIONS

Pursuant to 35 U.S.C. §202(c), it is hereby acknowledged that the U.S. Government has certain rights in the invention described herein, which was made in part with funds from the National Institute of Health.

BACKGROUND OF THE INVENTION

The present invention relates to a method of assessing a diabetic patient's risk of experiencing a diabetes-associated pathologic condition, or the efficacy of therapeutic intervention in prevention of diabetic complications, by measuring the levels of certain, newly discovered, phosphorylated carbohydrates present in the cellular components of biological materials, such as red blood cells. Some of these metabolites are unstable, and decompose to produce reactive, toxic materials, such as 3-deoxyglucosone produced from fructose-3-phosphate. As will appear below, these metabolites have a demonstrable toxic effect on red blood cells. In addition, compounds such as 3-deoxyglucosone, due to their uncharged character, are able to diffuse out of the red blood cells into the patient's biological fluids such as blood plasma, lymph fluids and interstitial fluids where they then react with proteins. Such reactions, known as non-enzymatic glycosylation or Maillard reactions, lead to the formation of advanced glycosylation end products (AGE) and crosslinking of long lived proteins such as collagen and basement membrane components.

The reaction of reducing sugars with proteins to form stable adducts is relatively well established. In 1912, Maillard experimentally identified the reaction responsible for the formation of the brown pigments often observed during the cooking of food. By heating glucose, as well as certain other saccharides, with various amino acids, Maillard was able to form stable brown pigments. L. C. Maillard *C. R. Acad. Sci.*, 154:66 (1912).

The mechanism of this non-enzymatic glycosylation was elucidated by food chemists in subsequent years; because the resultant browning changes the flavor and nutritional value of foods, especially during storage and processing (e.g., heating), the food industry quickly recognized the economic importance of this reaction and the need to understand and manipulate it. Further insights concerning the reaction were gained after the more recent discovery that the Maillard reaction occurs in vivo, including in humans, and is implicated in aging and diabetes-associated pathologic conditions.

The Maillard reaction, as currently understood, may be divided into early and advanced stages. It is initiated by the reversible non-enzymatic condensation of a reducing sugar with a free amino group of a protein, nucleic acid, or amine to form a Schiff base. The Schiff base reversibly undergoes an acid catalyzed Amadori rearrangement to give a stable ketamine compound called the Amadori product (also called the early glycosylation or early Maillard end-product). This early stage of the reaction is often termed non-enzymatic glycosylation or glycation. Although coined to describe the reaction wherein glucose is the sugar substrate, here and throughout this application the terms "non-enzymatic glycosylation", "non-enzymatic glycation" and similar terms are used interchangeably to refer to the early stages of the Maillard reaction, regardless of whether the sugar substrate is glucose or some other reactive reducing sugar (e.g., fructose). In the advanced stage, the Amadori product irreversibly breaks down to a variety of reactive α-dicarbonyl compounds, also known as breakdown products, the relative amounts of which are determined by reaction conditions. These reactive dicarbonyls, which include the deoxyglucosones, are generally more reactive than the parent sugar toward free amino groups. These compounds further react with free amino groups to form various stable, UV absorbent, often fluorescent, cross-linked products (also called advanced glycosylation or advanced Maillard end-products). In some cases, the reaction appears to terminate at this point, but often, these end-products further polymerize to give the characteristic brown pigments. See generally, *The Maillard Reaction in Aging, Diabetes and Nutrition*, J. W. Baynes and V. M. Monnier, eds. (Liss, New York, 1989).

The similarities between the pathologies arising from aging and those resulting from diabetes have been extensively reported. Studies have shown that many diabetes-associated pathologic conditions are clinically very similar to the pathologies normally associated with aging. Here and throughout this application the term "diabetes-associated pathologic condition" and synonymous terms are meant to include the various well-known neuropathic, nephropathic, macroangiopathic as well as other complications of diabetes. These conditions include, but are not limited to, the following representative examples. In cataracts are found to occur 10-15 years earlier than in normal individuals. Arteries and joints prematurely stiffen, lung elasticity and vital capacity prematurely decrease, and atherosclerosis, myocardial infarction and strokes occur more frequently in diabetics than in age-matched nondiabetic individuals. Diabetics are more susceptible to infection, and are more likely to have hypertension, accelerated bone loss, osteoarthritis and impaired T-cell function at a younger age than nondiabetics. Id., at p. 5 and references cited therein.

The similarities between aging and diabetes-associated pathologic conditions would appear to suggest a common mechanistic rationale. A variety of mechanisms have been proposed as a common biochemical basis for both diabetes-associated pathologic conditions and aging, however, none of the proposed mechanisms has proven especially satisfactory. The hypothesis most strongly supported by data from human subjects is premised on a non-enzymatic glycosylation mechanism. This hypothesis states that the aging process and diabetes-associated pathologic conditions, such as those described above are caused, at least in part, by protein modification and cross-linking by glucose and glucose-derived metabolites via the Maillard reaction. V. M. Monnier, R. R. Kohn, A. Cerami, *Proc. Natl. Acad. Sci. U.S.A.*, 81:583 (1984); J. H. Lee, D. H. Shin, A. Lupovitch, D. X. Shi, *Biochem. Biophys. Res. Commun.*, 123:888 (1984). In the case of diabetic complications, the reaction is thought to be kinetically accelerated by the chronic hyperglycemia often associated with diabetes. Evidence supporting this mechanism includes the fact that long-lived proteins such as collagen and lens crystallins from diabetic subjects are significantly more glycosylated, and therefore, modified and cross-linked, than those from age-matched normal controls. Thus, the unusual incidence of cataracts in diabetics at a relatively early age is explainable, according to the glycosylation hypothesis, by the increased rate of modification and cross-linking of lens crystalline, which is driven by hyperglycemia. Similarly, the early onset of joint and arterial stiffening as well as loss of lung capacity observed in diabetics may be explained by the increased rate of modification and cross-linking of collagen, the key structural protein. Because these proteins are long-lived, the consequences of glycosylation tend to be cumulative, and thus more drastic than in proteins with a relatively high turnover.

Methods for monitoring metabolic control in diabetic patients by measurement of glycosylation end-products are known. The concentration of glycosylated hemoglobin is known to reflect mean blood glucose concentration during the preceding several weeks. U.S. Pat. No. 4,371,374, issued to A. Cerami et al., described a method for monitoring glucose levels by quantitation of the degradation products of glycosylated proteins, more specifically non-enzymatically glycosylated amino acids and peptides, in urine. The described method utilized the affinity of alkaline boronic acids for forming specific complexes with the coplanar cis-diol groups found in glycosylation end-products to separate and quantitate such end-products.

U.S. Pat. No. 4,761,368, issued to A. Cerami, describes the isolation and purification of a chromophore present in browned polypeptides, e.g., bovine serum albumin and poly-L-lysine. The chromophore, 2-(2-furoyl)-4(5)-2(furoyl)-1H-imidazole (FFI) is a conjugated heterocycle derived from the condensation of two molecules of glucose with two lysine-derived amino groups. The '368 patent further describes the use of FFI in a method for measuring "aging" (the degree of advanced glycosylation) in a protein sample wherein the sample "age" is determined by measuring the amount of the above-described chromophore in the sample and then comparing this measurement to a standard (a protein sample having an amount of FFI which has been correlated to the "age" of the sample).

A difficult problem encountered in the medical treatment of diabetes has been the inability to identify those diabetic patients who are at risk of experiencing some diabetes-associated pathologic condition, so as to effect timely intervention. However, recent reports have identified certain diabetes-associated metabolites in mammalian lens tissue previously undetected in vivo, namely, sorbitol-3-phosphate (S3P) (Szwergold, B. S., Kappler, F., Brown, T. R., Pfeffer, P., and Osman, S. F., *J. Biol. Chem.*, 264:9278 (1989) and fructose-3-phosphate (F3P) (Szwergold, B. S., Kappler, F., and Brown, T. R., *Science*, 247:451 (1990). The concentrations of both of these compounds in the lens of the diabetic rat have been found to increase substantially after onset of the disease. Gonzalez, R. G., *Mag. Res. Med.*, 6:435 (1988). Our research has shown that F3P is a relatively potent glycosylating agent which, in addition, is quite labile, especially in the presence of amines, breaking down to produce an even more potent Maillard glycosylating and cross-linking agent, 3-deoxyglucosone (3dG). Kato, M., Hayase, F., Shin, D. B., Oimomi, M. and Baba, S. (1989), *The Maillard Reaction in Aging, Diabetes and Nutrition*, J. W. Baynes and V. M. Monnier, eds, at 69-84 (Liss, New York, 1989).

Since, as described above, increased glycosylation of proteins in diabetic patients is well known and appears to be casually related to various pathologic conditions, the increase in F3P concentration in diabetic rat lenses suggests that F3P and 3dG may be casually linked to the observed enhanced glycosylation.

SUMMARY OF THE INVENTION

The present invention is the outgrowth of several recent related discoveries. Specifically, we have discovered that both F3P and S3P are produced in normal human erythrocytes and that a significant proportion of erythrocyte samples taken from diabetic patients show elevated levels of these metabolites. We have also, surprisingly, found that among diabetic patients, a significant number of those having elevated F3P/S3P levels also manifested diabetes-associated pathologic conditions. Additionally, we have discovered that both normal and diabetic human erythrocytes contain two compounds, referred to herein as Compound a and Compound b, which have been partially characterized, and which appear to belong to the same chemical class as S3P and F3P. We have further discovered that Compounds a and b, as well as S3P, are present at elevated levels in a significant number of diabetic patients, and further, that when the sum of the blood concentrations of Compounds a and b exceeds the blood concentration of S3P in diabetic patients, virtually all of these patients manifest overt clinical symptoms of diabetes-associated pathologic complications.

In accordance with the present invention, there is provided a method for assessing a diabetic patient's risk of experiencing a diabetes-associated pathologic condition by measuring the level of at least one analyte in a biological fluid of the patient, the analyte being a metabolically-derived carbohydrate phosphorylated at a secondary hydroxyl group.

More specifically, the method of the invention entails assessing a diabetic patient's risk of experiencing a diabetes-associated pathologic condition by measuring the levels of metabolically-derived fructose-3-phosphate or sorbitol-3-phosphate, comparing the measured level(s) of such metabolite(s) to a predetermined threshold or standard and determining the relative degree of risk on the basis of such comparison.

In a particularly preferred embodiment of the invention, a diabetic patient's risk of experiencing a diabetes-associated pathologic condition is assessed by determining the ratio of the sum of the concentrations of Compounds a and b to the concentration of S3P in a sample of the patient's blood. The method of the invention is also useful for assessing the efficacy of therapeutic intervention in prevention and treatment of diabetic complications.

The method of the present invention is based on the detection and relative quantitation, using well-known techniques, of at least one analyte present in the biological cells or tissue of a diabetic patient. The analyte is a metabolically-derived carbohydrate phosphorylated at a secondary hydroxyl group. The level of the measured analyte is compared to a predetermined threshold level of the analyte established for normal, that is, nondiabetic subjects. This comparison provides the basis for determining whether the diabetic patient has an increased or decreased risk of experiencing a diabetes-associated pathologic condition. Preferably, the analyte measured is S3P or F3P. Elevated levels of these analytes in a diabetic patient's erythrocytes, either individually or in combination, indicate an increased risk of experiencing a diabetes-associated pathologic condition. Most preferably, the analytes measured are S3P and two compounds which are believed to be of the same chemical class as S3P, Compound a and Compound b. Although the precise chemical structures of Compounds a and b have not yet been elucidated, they are readily identifiable by certain known physicochemical characteristics, which are described below. Once the relative levels of these three metabolites have been quantitated, the diabetic patient's risk of experiencing a diabetes-associated pathologic condition is determined by the ratio expressed in Equation 1.

$$\frac{[a] + [b]}{[S3P]} = X \qquad \text{EQ. 1}$$

If X exceeds the established threshold, the patient has an increased risk of experiencing a diabetes-associated pathologic condition. Conversely, if X is less than the threshold value, the patient is not more likely to experience such a condition than a nondiabetic person.

BRIEF DESCRIPTION OF THE DRAWINGS

FIGS. 4A-D shown scattergram plots of the concentrations of sorbitol-3-phosphate (FIG. 4A), fructose-3-phosphate (FIG. 4B), Compound a (Panel C) and Compound b (FIG. 4D) in normal test subjects and in diabetics.

DETAILED DESCRIPTION OF THE INVENTION

As noted above, we have detected by $^{31}$P NMR spectroscopy four novel phosphorylated metabolites in human erythrocytes. Two of these metabolites were identified as S3P and F3P. Spectra illustrating the detection of these compounds and the identifications of F3P and S3P are shown in FIGS. 1A-D.

As was the case with the spectra shown in FIG. 2 and FIGS. 3A-C, these data were obtained at room temperature at 161.98 MHz on the AM-400 Bruker NMR Spectrometer using a standard 10 mM NMR probe. Spectra were collected in 250-5000 scans using a 60° pulse and a 1.5 sec. repetition rate.

Identifications of peaks in these spectra are as follows: a—Compound a; b—Compound b; S3P—sorbitol-3-phosphate; F3P—fructose-3-phosphate; 2,3 DPG-2,3 diphosphoglycerate; Pi—inorganic phosphate, $\gamma$ $\alpha,\beta$(NTP) - $\gamma,\alpha,\beta$ phosphates of adenosine triphosphate (nucleoside triphosphates).

Our experimental evidence suggests that all four of these compounds are produced in the erythrocytes by phosphorylating an exogenously supplied parent carbohydrate at a secondary hydroxyl (C3 hydroxyl in the case of S3P and F3P). This is most clearly illustrated in FIG. 2 which shows the time course of the accumulation of F3P in erythrocytes exposed to fructose. Cells were incubated at 37° C. in a physiological medium containing 5 mM glucose and 30 mM fructose. At the times indicated in the description of FIG. 2, aliquots of cells were removed and $^{31}$P NMR spectra were collected. As is evident from these spectra, under the conditions employed erythrocytes rapidly accumulate F3P resulting, after four hours of incubation, in approximately 1 mM intracellular concentration of F3P.

Figure 1A:
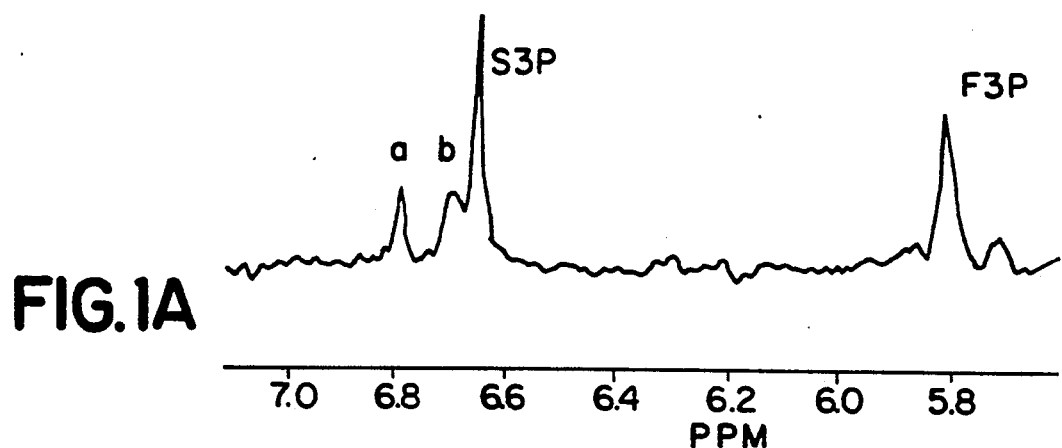
FIG. 1A shows the 5.5 to 7.0 region of a proton decoupled $^{31}$P NMR spectrum.
Figure 1B:
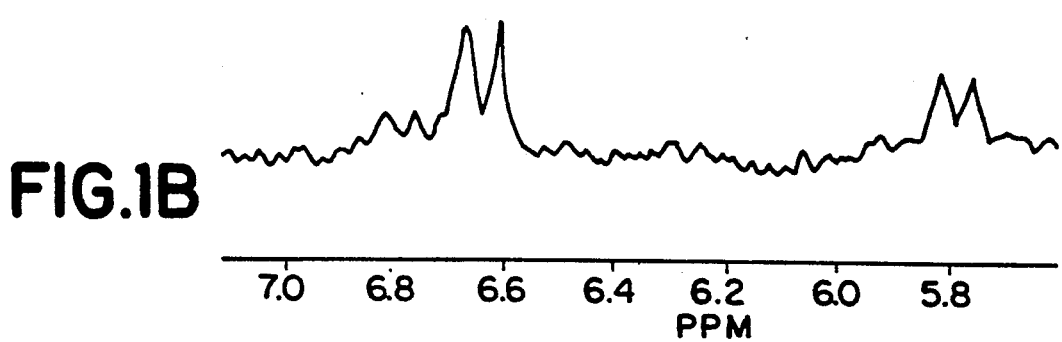
FIG. 1B shows the same spectral region obtained without proton decoupling. The splitting of peaks into doublets is due to the spin-spin coupling between the nucleus of phosphorus and a proton located on the adjacent carbon.
Figure 1C:
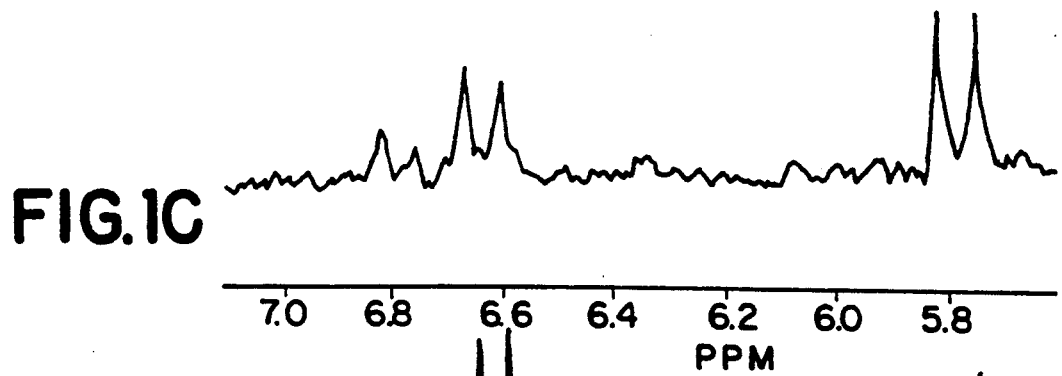
FIG. 1C illustrates the identification of the peaks at 5.8 ppm as fructose-3-phosphate through the addition of synthetic fructose-3-phosphate to the solution whose spectrum is shown in FIG. 1B. Similarly, in FIG. 1D, addition of synthetic sorbitol-3-phosphate to the same solution whose spectrum is shown in Panel C identified the large peaks at 6.6 ppm as being sorbital-3-phosphate. It should be noted that the synthetic and natural materials continue to co-resonate throughout a pH titration of the solution.
Figure 1D:
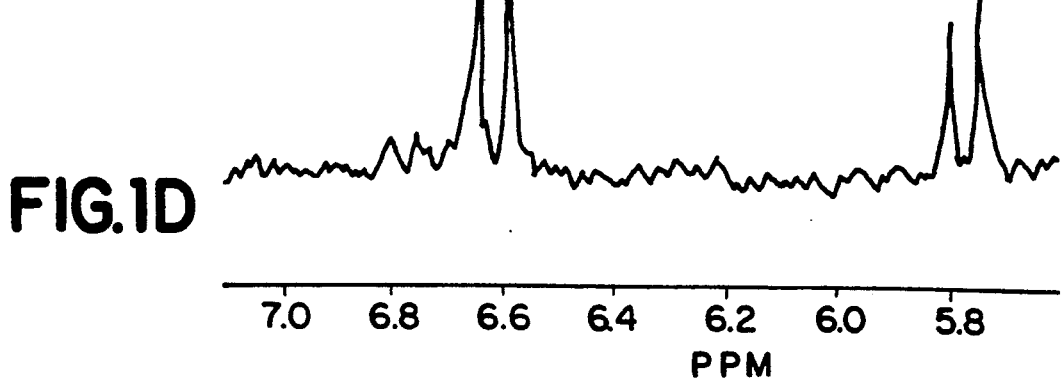
FIGS. 1 A-D are $^{31}$P NMR spectra of an extract of normal human erythrocytes.
Figure 2:
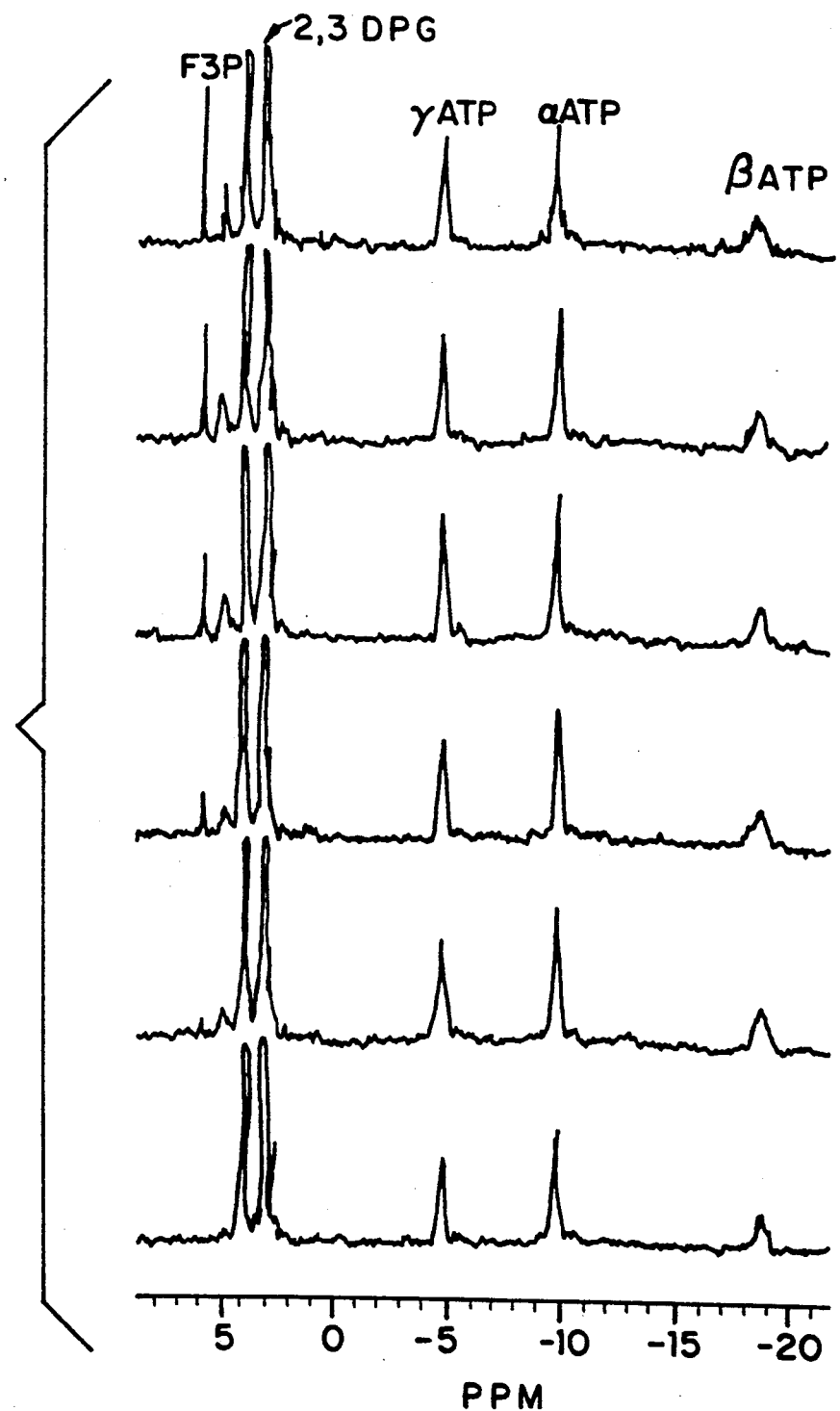
FIG. 2 is a related series of $^{31}$P NMR spectra, as indicated by the bracket reflecting production of fructose-3-phosphate by erythrocytes from exogenous fructose over a period of four hours. Starting with the bottom most spectrum (time=0) and going up, the other spectra were recorded after 0.5 hr, 1 hr, 2 hrs, 3 hrs, and 4 hrs, respectively.
Figure 3A:
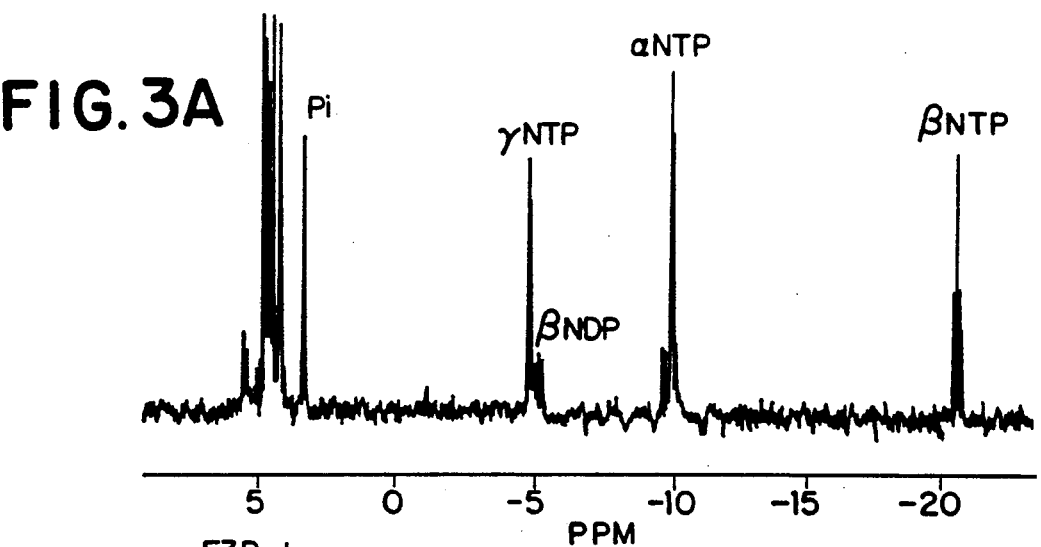
FIGS. 3A-C are $^{31}$P NMR spectra showing the effect of fructose-3-phosphate on red cell viability.
Figure 3B:
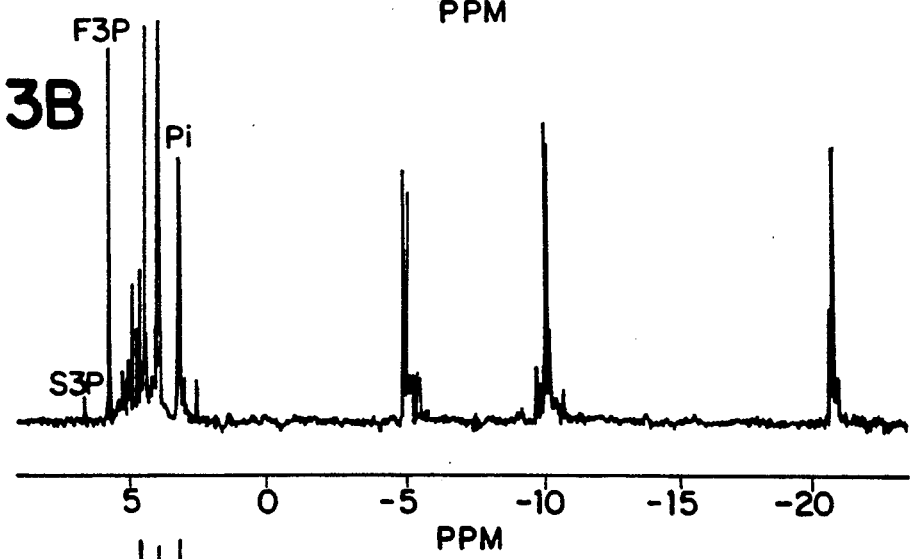
Figure 3C:
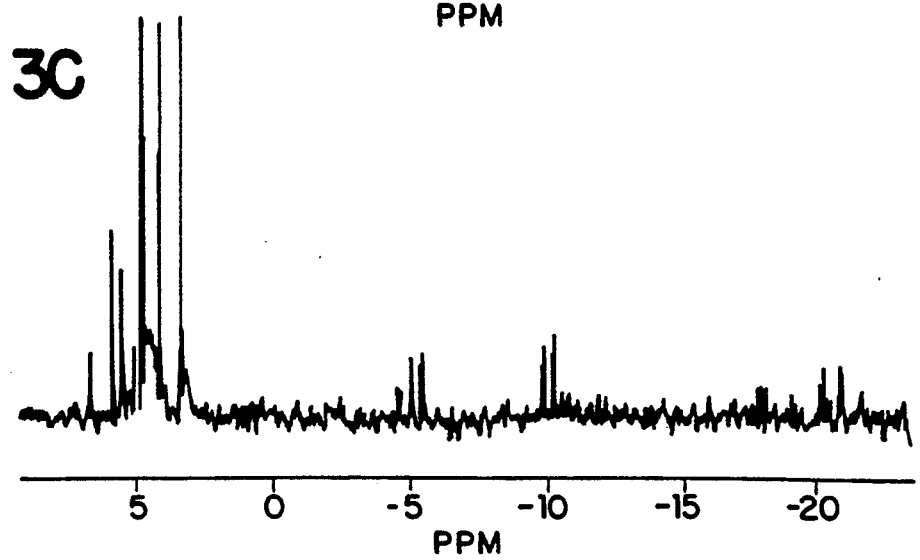

Our previous experiments with the diabetic rat lens suggests that such high concentrations of F3P may be toxic. FIGS. 3A-C illustrates the results of an experiment which confirms that this indeed is the case for erythrocytes. FIG. 3A shows a $^{31}$P NMR spectrum of erythrocytes following a 36 hour incubation at 37° C. in a physiological medium containing 5 mM glucose as the only carbon source. This spectrum is identical to a spectrum of freshly isolated erythrocytes which, together with independent microscopic examination of these cells, suggests that such an incubation produces no deleterious effects on these cells. In contrast, when erythrocytes are "loaded" with F3P (FIG. 3B) and then incubated for 12 hrs. in a fructose-free medium, identical to that used for the cells in FIG. 3A, there occurs a dramatic decrease in the concentration of ATP (FIG. 3C) accompanied by extensive hemolysis of the cells. This phenomenon indicates very strongly that F3P is indeed a toxic agent which, at sufficiently high concentration, leads to an irreversible decline in cell function and ultimately to cell death.

While the toxic potential and precise structures of compounds a and b are not known, they have many characteristics in common with S3P and F3P, such as unique chemical shifts, large $^1$H-$^{31}$P spin-spin coupling constants and unusually low pKa' values (see Table 1). In these properties, Compounds a and b differ substantially from other phosphomonoesters and thus appear to belong to the same class of compounds as S3P and F3P. As can be seen in FIGS. 4A-D, the concentrations of these metabolites are significantly elevated in many diabetic patients, when compared to normal individuals.

Figures 5A, 5B:
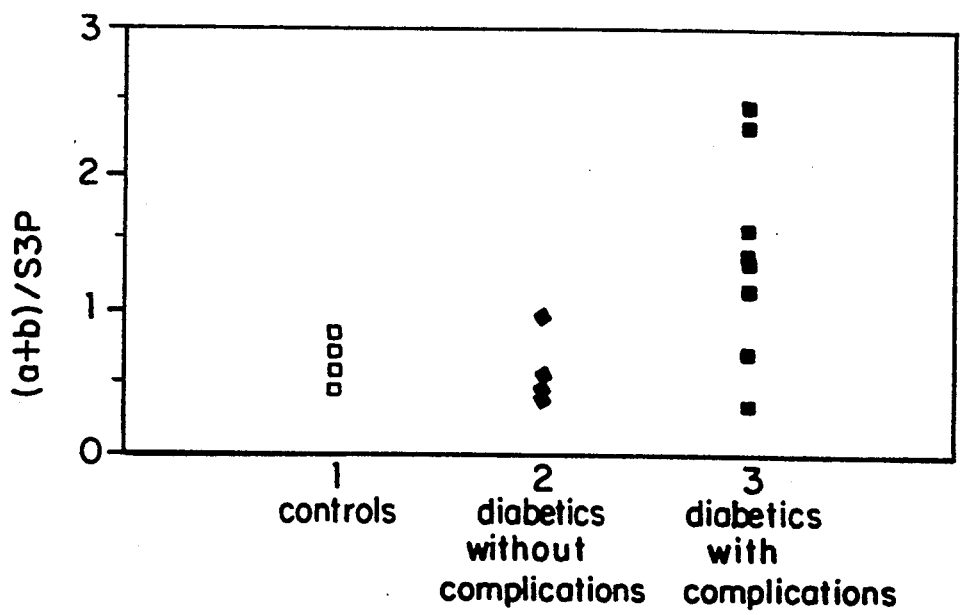
FIG. 5A is a scattergram plot of the ratio of the concentrations of Compounds a plus b to sorbitol-3-phosphate ([a]+[b]/[S3P]) in normal subjects (controls), diabetics without complications and diabetics with complications.
FIG. 5B shows the same data as in the scattergram of FIG. 5A, but represented as a truth table showing the correlation between the ratio, [a]+[b]/[S3P] and the presence or absence of diabetic complications. This correlation was shown to be significant at the p<0.03 level by an exact two tailed Fisher analysis of significance.

There is a good correlation between these elevated concentrations and the presence of clinical symptoms of diabetic complications such as retinopathy, peripheral neuropathy and peripheral vascular disease. This correlation is especially striking when one compares the sum of the concentrations of compounds a and b with the concentration of S3P ([a]+[b]/[S3P]). Considered with reference to this ratio, the data shown in FIGS. 5A and B indicates that there is a clear threshold for the appearance of diabetic complications. This preliminary data suggests that an appropriate threshold may be a ratio of [a]+[b]/[S3P] near 1.0, for purposes of distinguishing between diabetics at risk for complications and those who are not at an increased risk. As can be seen from FIG. 5B, differentiation between the two groups of diabetics is highly significant and specific.

Accordingly, we propose a measurement of the concentrations of these metabolites from erythrocytes of diabetic patients which will enable the clinician to assess the relative risk of a patient developing these complications and to evaluate the efficacy of treatment in preventing and/or ameliorating these complications. The assay entails drawing a small amount of venous blood (5-20 ml) and then measuring the concentration of the above-mentioned metabolites in the erythrocytes. The measurement of concentrations may be carried out by one of several methodologies indicated below in Examples 1, 2 and 3. Based on the results of this analysis, the ratio of the concentrations of compounds a and b to the concentration of S3P can be calculated. If this ratio is determined to be low (i.e., <1), our data suggests that this particular patient is at a relatively low risk for developing complications. Conversely, if the ratio is high (i.e. >1), this will be an indication that this particular patient has a relatively greater risk for developing complications and will have to be followed and treated more aggressively than a patient at relatively low risk.

TABLE 1

| Compound | $^{31}$P NMR Chemical Shift (at pH 7.5) | $^1$H-$^{31}$P Coupling (Hz) | pK$_a$ |
|---|---|---|---|
| S3P | 6.59 | 10.5 | 5.4 |
| F3P | 5.76 | 9.8 | 5.6 |
| Compound a | 6.63 | 9.5 | 5.5 |
| Compound b | 6.74 | 9.5 | 5.5 |

The following examples are provided to describe the invention in further detail; they are intended to illustrate and not to limit the invention.

EXAMPLE 1

NMR Assay

A 20 ml sample of venous blood is drawn into two 10 ml heparin vacutainer tubes. The sample is then transferred to a 50 ml plastic centrifuge tube and centrifuged at 10,000 G for 10 minutes at 4° C.

Supernatant plasma is removed and the cell pellet is homogenized for one minute in a 4× volume of 10% cold perchloric acid using a mechanical homogenizer such as the Tissuemiser TM. Cell debris is removed by centrifugation at 10,000 G for 10 minutes. Supernatant is transferred to a clean centrifuge tube and its pH adjusted to neutral using cold KOH. The precipitated potassium perchlorate is removed by centrifugation as above, followed by lyophilization of the supernatant to dryness.

The dried powder thus obtained is then taken up in 1.3 ml of D$_2$ and 0.2 ml of 0.25M CDTA. The pH of the solution is adjusted to 7.5 and the sample is analyzed by $^{31}$P NMR on a high field spectrometer.

The quantification of the spectral peaks for the metabolites of interest may be normalized to red cell volume as determined from the total blood volume and the hematocrit or to the concentrations of 2,3 DPG which has been well established to be 5.17 mM in erythrocytes (Maida, N., Chang, H., Benesch, R., and Benesch, R. E. N. Engl. J. Med., 284:1239 (1971) and is not affected in diabetes (Tegos, C., and Beutler, E., J. Lab. Clin. Med., 96:85 (1980).

EXAMPLE 2

HPLC Assay

Figure 6:
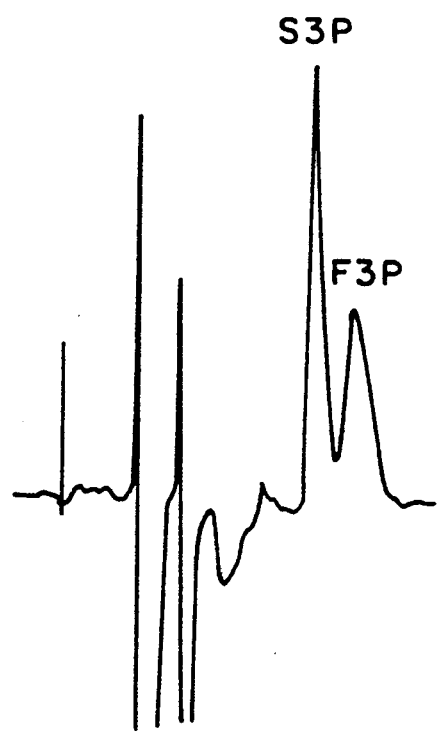
FIG. 6 is a refractive index detector tracing of synthetic S3P and F3P eluted from an HPLC ion exchange column. The compounds eluted 13.5 minutes and 15.5 minutes, respectively, after injection.

A blood sample is drawn and processed as described above up to the step after lyophilization. For HPLC analysis, the lyophilized powder is redissolved in 1 ml of distilled water and its pH adjusted to 5.8. The material is then loaded onto a strong anion exchange column, such as the Partisil ® Sax anion exchange column, and developed with an isocratic solvent system employing 0.5M ammonium acetate at pH 5.8. The materials eluting off the column may be detected and quantified using a differential refractive index detector (such as the Waters Associates Model 410). An example of the HPLC output from such an analysis is shown in FIG. 6.

An alternative HPLC assay involves derivatization of the metabolites of interest for UV detection. In carrying out such a procedure, dried lyophilized sample is dissolved in pyridine, cooled to 0° C. and benzoyl chloride is added to the resulting solution. After one hour, water is added and the solution is evaporated to dryness.

The dry sample containing benzoyl groups on the sugar hydroxyls is dissolved in an appropriate solvent such as trichloromethane or acetonitrile and applied to a reverse phase HPLC column, such as the Waters μ Bondapak C18. The system may be developed using a suitable gradient such as H$_2$O-methanol or H$_2$O-acetonitrile.

The introduction of the benzoyl group permits detection of the derivatized metabolites of interest using a UV detector at 254 nm.

EXAMPLE 3

Gas Chromatographic Assay

An aliquot of the dried perchloric acid extract is dissolved in 0.1 ml of pyridine and 0.1 ml of bis-(trimethylsilyl)-trifluoroacetamide containing 1% trimethylchlorosilane is added to the solution, which is stirred magnetically at room temperature for one hour. The derivatized extract is then analyzed on a gas chromatographic column such as a 4 foot×0.25 inch glass column packed with etched glass beads (80-100 mesh, Code 0201, Corning Glass Works, Corning, N.Y.), coated with 0.1% of Dow-Corning DC-710 silicon oil.

This procedure may be implemented following the identification and synthesis of Compounds a and b and a calibration of the system using the synthetic materials.

While various aspects of the present invention have been described and exemplified above in terms of certain preferred embodiments, various other embodiments may be apparent to those skilled in the art. The invention is, therefore, not limited to the embodiments specifically described and exemplified, but is capable of variation and modification without departing from the spirit of the invention, the full scope of which is delineated by the appended claims.

What is claimed is:

1. A method for assessing a diabetic patient's relative risk of experiencing a diabetes-associated pathologic condition, said method comprising the steps of:
    (a) measuring the levels of (i) a first compound, characterized by having a $^{31}P$ NMR shift of 6.63 at pH 7.5, an $^{1}H$-$^{31}P$ coupling of 9.5 Hz and a pKa of 5.5, (ii) a second compound, characterized by having a $^{31}P$ NMR shift of 6.74 at pH 7.5, an $^{1}H$-$^{31}P$ coupling of 9.5 Hz and a pKa of 5.5, and (iii) sorbitol-3-phosphate in said patient's red blood cells;
    (b) comparing the sum of said levels of measured first and second compounds to said level of measured sorbitol-3-phosphate; and
    (c) determining on the basis of said comparison whether said diabetic patient has an increased or a decreased risk of experiencing said diabetes-associated pathologic condition.

* * * * *